United States Patent
Andrus (10) Patent No.: US 10,314,956 B2
(45) Date of Patent: Jun. 11, 2019

(54) HOLLOW PLUG

(71) Applicant: HeartWare, Inc., Mounds View, MN (US)

(72) Inventor: Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 241 days.

(21) Appl. No.: 15/381,777

(22) Filed: Dec. 16, 2016

(65) Prior Publication Data

US 2017/0173236 A1   Jun. 22, 2017

Related U.S. Application Data

(60) Provisional application No. 62/269,217, filed on Dec. 18, 2015.

(51) Int. Cl.
*A61M 1/10* (2006.01)
*A61M 1/12* (2006.01)
(Continued)

(52) U.S. Cl.
CPC ... *A61M 1/1008* (2014.02); *A61B 17/320016* (2013.01); *A61F 2/2409* (2013.01);
(Continued)

(58) Field of Classification Search
CPC .. A61M 1/1008; A61M 1/1098; A61M 1/122; A61M 2210/125; A61M 2039/244;
(Continued)

(56) References Cited

U.S. PATENT DOCUMENTS

2004/0171905 A1   9/2004 Yu et al.
2007/0134993 A1   6/2007 Tamez et al.
(Continued)

FOREIGN PATENT DOCUMENTS

WO   2012019126 A1   2/2012
WO   2012119073 A1   9/2012
WO   2012158919 A2   11/2012

OTHER PUBLICATIONS

International Search Report and Written Opinion dated Jul. 27, 2017, for corresponding International Application No. PCT/US2016/067219; International Filing Date: Dec. 16, 2016 consisting of 16-pages.

*Primary Examiner* — Rex R Holmes
(74) *Attorney, Agent, or Firm* — Christopher & Weisberg, P.A.

(57) ABSTRACT

A mounting element defining a bore, the mounting element being configured to mount to an exterior surface of an organ of a patient. A one way valve sized to be received and retained within the bore of the mounting element is included, the one way valve having an open position and a closed position. The one way valve substantially occludes the bore when the valve is in the closed position. The one way valve is biased in the closed position. A plug having a lumen extending there through is included, the plug being configured to be releasably inserted through at least a portion of the one way valve. The plug is configured to transition the one way valve from the closed position to the open position and to maintain the one way valve in the open position when the plug is inserted within the bore.

18 Claims, 5 Drawing Sheets

(51) Int. Cl.
*A61B 17/32* (2006.01)
*A61F 2/24* (2006.01)
A61B 17/00 (2006.01)
A61M 39/24 (2006.01)

(52) U.S. Cl.
CPC ......... *A61F 2/2427* (2013.01); *A61M 1/1098* (2014.02); *A61M 1/122* (2014.02); *A61B 2017/00247* (2013.01); *A61B 2017/320052* (2013.01); *A61M 2039/244* (2013.01); *A61M 2210/125* (2013.01)

(58) Field of Classification Search
CPC ........... A61B 17/320016; A61B 2017/320052; A61B 2017/00247; A61F 2/2409; A61F 2/2427
See application file for complete search history.

(56) References Cited

U.S. PATENT DOCUMENTS

| | | | |
|---|---|---|---|
| 2015/0112120 A1* | 4/2015 | Andrus | A61M 1/1008 600/16 |
| 2016/0121033 A1* | 5/2016 | Cotter | A61M 1/1008 623/3.26 |

* cited by examiner

HOLLOW PLUG

CROSS-REFERENCE TO RELATED APPLICATION

This application is related to and claims priority to U.S. Provisional Patent Application Ser. No. 62/269217, filed Dec. 18, 2015, entitled HOLLOW PLUG, the entirety of which is incorporated herein by reference.

STATEMENT REGARDING FEDERALLY SPONSORED RESEARCH OR DEVELOPMENT n/a

TECHNICAL FIELD

The present invention relates to components and methods used for mounting devices such as ventricular assist devices and associated elements to the heart of a living subject.

BACKGROUND

The heart is sometimes incapable of providing sufficient pumping capacity to meet the needs of the body. The effects of this inadequacy can be alleviated by providing a mechanical pump referred to as a mechanical circulatory support device ("MCSD"). An MCSD can be implanted to supplement the pumping action of the heart, most commonly for an extended period of time such as several years.

An MCSD is most commonly connected to the left ventricle. In this arrangement, an inlet end of the pump, or an inlet cannula connected to the inlet end of the pump, is implanted in the wall of the ventricle, such as at the apex of the ventricle. An outlet cannula is connected between the outlet end of the pump and an artery such as the aorta. MCSDs which are connected to a ventricle commonly are referred to as ventricular assist devices or "VADs." During operation, the VAD assists the heart to pump blood from the left ventricle to the aorta.

The certain MCSDs are typically connected to the heart through the use of a mounting ring, as disclosed in U.S. Published Patent Publication Nos. 2004/0171905, 2007/0134993, and 2015/0112120, the disclosures of which are hereby incorporated by reference herein. A mounting ring has a body and a bore extending through the body, and also has features which can be used to attach the body to the outside of the heart wall so that the bore extends towards and away from the wall. For example, some mounting rings are equipped with a ring of fabric encircling the body, so that the mounting ring can be secured in place by suturing. Other mounting rings are equipped with barbs or other fasteners for attaching the body of the ring to the heart wall. Some mounting rings incorporate an element referred to as a gimbal which is pivotally mounted to the body of the mounting ring and which defines the bore of the mounting ring. The gimbal can be tilted to align the axis of the bore.

A cruciate cut is made in the heart wall within the bore of the mounting ring and a separate surgical tool is used to core a hole in the heart. The pump, or an inlet cannula connected to the pump, is then inserted through the hole into the heart and secured to the mounting ring. If the mounting ring is equipped with a gimbal, the gimbal can be tilted to align the axis of the pump or cannula with the anatomical features of the heart. The seal between the heart and mounting ring must be sufficiently tight to prevent blood loss from the heart. Also, the attachment between the heart and the ring must remain secure despite mechanical stresses and the attachment procedure should minimize damage to the wall of the heart.

SUMMARY

The application advantageously provides for a mounting kit including a mounting element defining a bore, the mounting element being configured to mount to an exterior surface of an organ of a patient. A one way valve sized to be received and retained within the bore of the mounting element is included, the one way valve has an open position and a closed position. The one way valve substantially occludes the bore when the valve is in the closed position. The one way valve is biased in the closed position. A plug having a lumen extending there through is included, the plug is configured to be releasably inserted through at least a portion of the one way valve. The plug is configured to transition the one way valve from the closed position to the open position and to maintain the one way valve in the open position when the plug is inserted within the bore.

In another aspect of this embodiment, the plug has a flange configured to provide for a maximum depth insertion of the plug within the bore.

In another aspect of this embodiment, the one way valve is one from the group consisting of a tri-leaflet valve, flap valve, butterfly valve, and duckbill valve.

In another aspect of this embodiment, the mounting element includes a ring defining an opening, the ring being configured to be anchored to the exterior surface of the organ.

In another aspect of this embodiment, the mounting element includes an adaptor sized to be received within the opening of the ring, the adaptor defining an aperture, the opening of the ring being substantially co-axial when then adapter is received within the opening of the ring.

In another aspect of this embodiment, the adaptor defines an annular wall defining a plurality of slits, and wherein at least a portion of the annular wall is flexible.

In another aspect of this embodiment, the adaptor is configured to receive and retain at least one from the group consisting of a pump and a cannula within the bore.

In another aspect of this embodiment, the mounting element further includes gimbal sized to be received and retained within the aperture of the adaptor, the gimbal defining an orifice, the gimbal being configured to tilt the alignment of the orifice with respect to the aperture of the adaptor when the gimbal is received within the aperture of the adaptor.

In another aspect of this embodiment, the gimbal is substantially co-axial to the adaptor when the gimbal is received within the aperture of the adaptor.

In another aspect of this embodiment, the gimbal defines an outer wall surrounding the orifice, and wherein at least a portion of the outer wall is flexible.

In another aspect of this embodiment, the organ is the heart.

In another aspect of this embodiment, the plug is configured to releasably mount to a cutting device.

In another embodiment, a method of creating an access way into the heart includes mounting a mounting element to external surface of the heart. The mounting element defines a bore sized to receive a one way valve disposed therein. The one way valve defines an open position and a closed position. The one way valve substantially occludes the bore when the valve is in the closed position. The valve is biased in the closed position. A plug is inserted through the one way valve, the plug defines a lumen there through and is configured to transition the one way valve from the closed position to the open position and to maintain the one way valve in the open position when the plug is inserted within the bore. The external surface of the heart is cut through the lumen of the plug In another aspect of this embodiment, the method further includes removing the plug from the bore after cutting the external surface of the tissue and transitioning the one way valve from the open position to the closed position.

In another aspect of this embodiment, inserting the plug through the bore further includes advancing a cutting device having the plug releaseably coupled to its distal end through the bore.

In another aspect of this embodiment, the plug has a flange configured to provide for a maximum depth insertion of the plug within the bore.

In another aspect of this embodiment, inserting the plug further includes inserting the plug until the flange is pressed against the one way valve.

In another aspect of this embodiment, the mounting element further includes an adaptor defining an aperture sized to be received within the bore, the adaptor being configured to receive and retain at least one from the group consisting of a pump and a cannula within the bore.

In another aspect of this embodiment, the mounting element further includes a gimbal defining an orifice, the gimbal being sized to be received within the bore, the gimbal being configured to tilt the alignment of the orifice with respect to the aperture of the adaptor when the gimbal is received within the aperture of the adaptor.

In yet another embodiment, the mounting kit includes a ring defining an opening. The ring is configured to be anchored to the exterior surface of the left ventricle of a user's heart. An adaptor defining an aperture is included, the adaptor is sized to be received within the opening of the ring. The adaptor is configured to receive and retain at least one from the group consisting of a pump and a cannula within the bore. A gimbal defining an orifice is included, the gimbal is sized to be received within the aperture of the adaptor. The gimbal is configured to tilt the alignment of the orifice with respect to the aperture of the adaptor when the gimbal is received within the aperture of the adaptor, the ring, the adaptor, and the gimbal being substantially co-axial when the adaptor is inserted within the opening of the ring, and the gimbal is inserted within the aperture of the adaptor. A one way valve sized to be received and retained within orifice of the gimbal is included, the one way valve has an open position and a closed position. The one way valve substantially occludes the opening, the aperture, and the orifice when the valve is in the closed position. The one way valve is biased in the closed position. A plug having a lumen extending there through is included, the plug is configured to be releasably inserted through at least a portion of the one way valve. The plug is configured to transition the one way valve from the closed position to the open position and to maintain the one way valve in the open position when the plug is inserted within the valve. The plug includes a flange configured to provide for a maximum depth insertion of the plug within the valve.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 1:
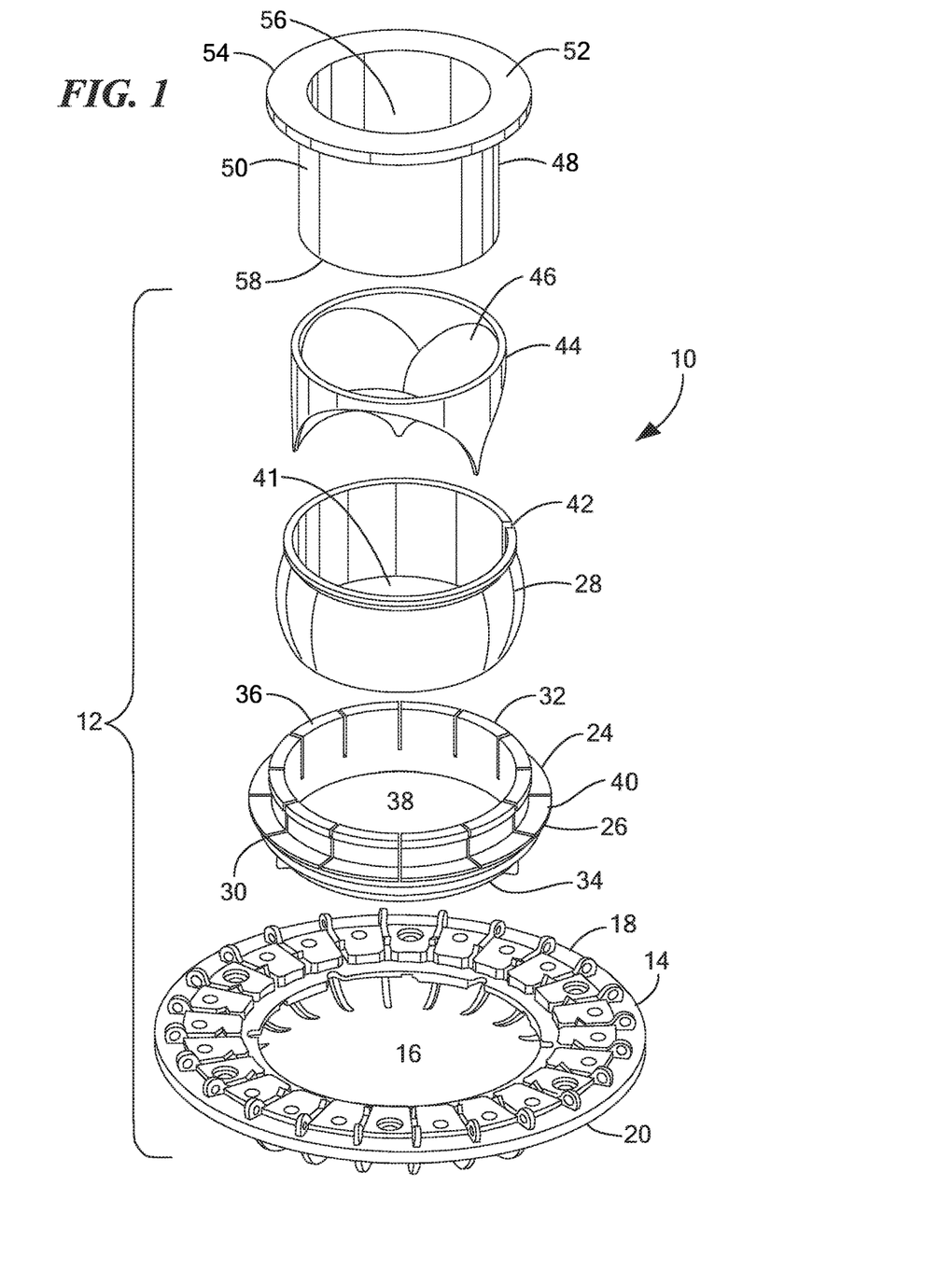
FIG. 1 is an exploded view of a mounting kit in accordance with one embodiment of the current invention.

Now referring to the drawings in which like reference designators refer to like elements, there is shown in FIG. 1 an exemplary mounting kit constructed in accordance with principles of the present application and designated generally as "10." The mounting kit 10 includes a mounting element 12 configured to mount to the exterior surface or tissues or organs of a human or animal patient, and in a particular example, the left ventricle of the heart. The particular mounting element 12 depicted in FIG. 1 is as shown and described in greater detail in the aforementioned U.S Published Patent Publication No. 2015/0112120. For example, the mounting element 12 may include a ring 14 configured to be pressed against and anchored to the external surface of the organ or tissue to be mounted. The ring 14 may be define any shape or size, may be substantially flat or alternatively define a substantially toroidal shape. The ring 14 defines an opening 16 extending from a proximal side 18 of the ring 14 to a distal side 20 of the ring 12. A plurality of anchors 22 are positioned about the opening 16 of the ring 14 to secure the distal side 20 to the tissue or organ. While the ring 14 is shown as including a plurality of anchors 22 to mount the ring 14 to tissue or organs, it is contemplated that any anchoring mechanism may be incorporated with the ring 14, for example, loops or hooks for application of sutures, barbs, pins, tissue adhesive, and the like to mount the ring 14 to the target tissue or organ. Although not shown, the ring 14 may have a fabric element extending around its circumference, so that the mounting element 10 can be secured in place by suturing the fabric element to the surface of an organ.

The mounting element 12 further includes an adaptor 24 configured to receive and retain at least one from the group consisting of a pump and a cannula and configured to be received and retained within the opening 16 of the ring 14. In the embodiment shown in FIG. 1, the adaptor 24 includes an annular wall 26 and an optional gimbal 28 sized to be received within the interior of the adaptor 24. The adaptor 24 may be formed integrally with the ring 14 as a unitary body or may be distinct components. In one configuration, the annular wall 26 defines plurality of slits 30 extending from a proximal side 32 toward a distal side 34. The slits 30 may be configured to separate at least a portion of the annular wall 26 into tabs 36. The adaptor 24 may further define an aperture 38 surrounded by of the annular wall 26. When the adaptor 24 is received and retained within the opening 16, the aperture 38 and the opening 16 may be substantially co-axial. The annular wall 26 may be configured to transition from a first state where the slits 30 separate the tabs 36 by a first distance to a second state where the slits 30 separate the tabs 36 by a second distance less than the first distance, so as to constrict the aperture 38. Thus, at least a portion of the annular wall 26 is flexible to reduce the size of the aperture 38. In one configuration a rim 40 extends from the annular wall 26 which may provide a shelf for a clamp (not shown). The clamp may extend around the outside of the adaptor 24 and arranged so that tightening the clamp compresses the annular wall 26 and thus constricts aperture 38 and constricts the gimbal. This clamping arrangement can be used to hold a pump or cannula in place within the aperture 38.

The gimbal 28 is adapted to fit within the aperture 38 of the adaptor 24. In one configuration the gimbal 28 has a semi-spherical outer contour and defines an orifice 41 and a relief 42 extending through the wall of the gimbal 28. The gimbal 28 is sized and configured to be received and retained within the opening aperture 38 of the adaptor and opening 16 of the ring 14, so that the gimbal 28 can pivot to tilt the axis of the orifice 41 relative to the opening 16 of the ring 14 and the aperture 38 of the adaptor 24. The relief 42 is configured to allow the outer wall of the gimbal 28 to expand and contract beyond its resting configuration, thus providing at flexibility to the outer wall.

Continuing to refer to FIG. 1, the mounting element 12 may further include a one way valve 44 formed from a resilient, biocompatible material, which sized and configured to be received within orifice 41 of the gimbal 28. The one way valve 44 may be a tri-leaflet valve, flap valve, butterfly valve, duckbill valve, which permits the flow of fluid in one direction and prevents the flow of fluid in a second direction. In the embodiment shown in FIG. 1, valve 44 has leaves 46 which are shown in the open position. In an exemplary configuration, the leaves 46 of valve 44 are biased in a closed position in which the orifice 41 is substantially occluded. For example, the leaves 46 of the valve 44 are biased to abut one another to substantially occlude the orifice of 40 of the gimbal 28. However, when a solid object is inserted through the orifice 41 of the gimbal 28, the leaves 46 of the valve 44 transition to the open position to allow passage of the object.

Continuing to refer to FIG. 1, a plug 48 is sized and configured to be inserted through the valve 44 and/or through the opening 16, the aperture 38, and/or the orifice 41 that cooperate to define a bore through the mounting element 10. In the embodiment shown in FIG. 1, the plug 48 has a body 50, which in one configuration is tubular with a flange 52 on a proximal end 54. The outside diameter of the body 50 is smaller than the inside diameter of orifice 41 in the gimbal 28 whereas flange 52 has a diameter greater than the inside diameter of orifice 41. The plug 48 has a lumen 56 extending from the proximal end 54 to its distal end 58. In one configuration, the plug 48 is manufactured of a material such as a polymer or metal, but may be any biocompatible material. In one configuration, the distal end 58 of the plug 48 has smooth atraumatic surfaces and rounded or chamfered edges so that the plug 48 can be inserted into the valve 44 without cutting or tearing the leaves 46 of valve 44.

Figure 2:
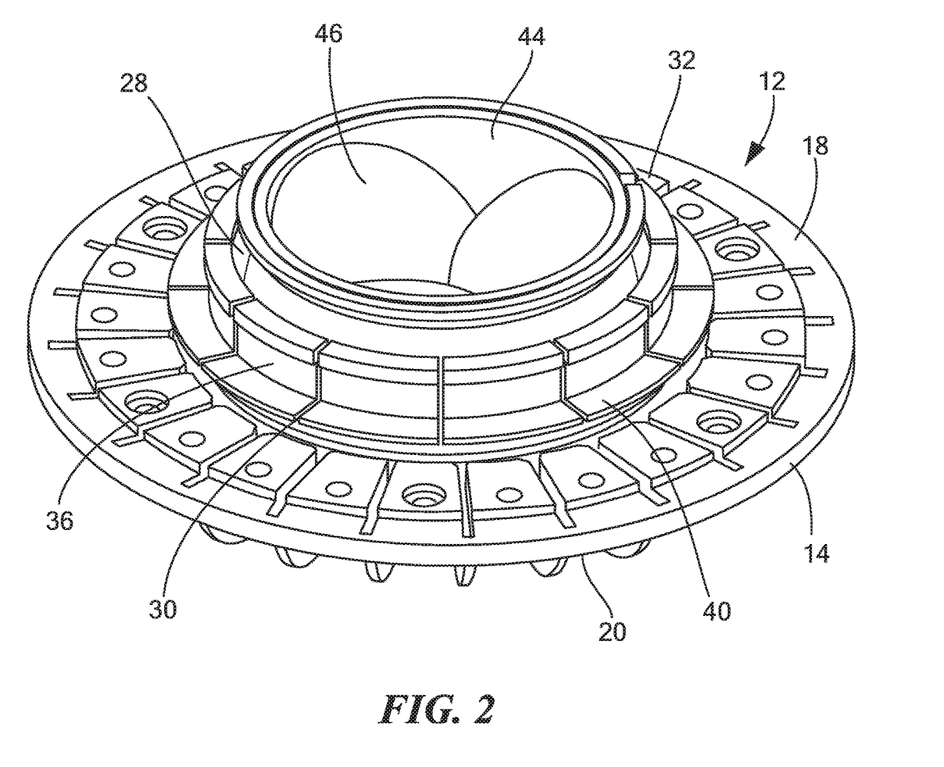
FIG. 2 is a perspective view of the mounting element and the one way valve shown in FIG. 1.

Referring now to FIG. 2, when assembled, the mounting element 12, adaptor 24, gimbal 24, and valve 44 are nested together to define a bore there through. In one configuration, the valve 44 is biased toward the closed position and the bore through the mounting element 12 is substantially occluded. The configuration shown in FIG. 2, is one representation of the mounting element 12 as it is affixed to tissue. In other configurations, the gimbal 28 may be tilted.

Figure 3:
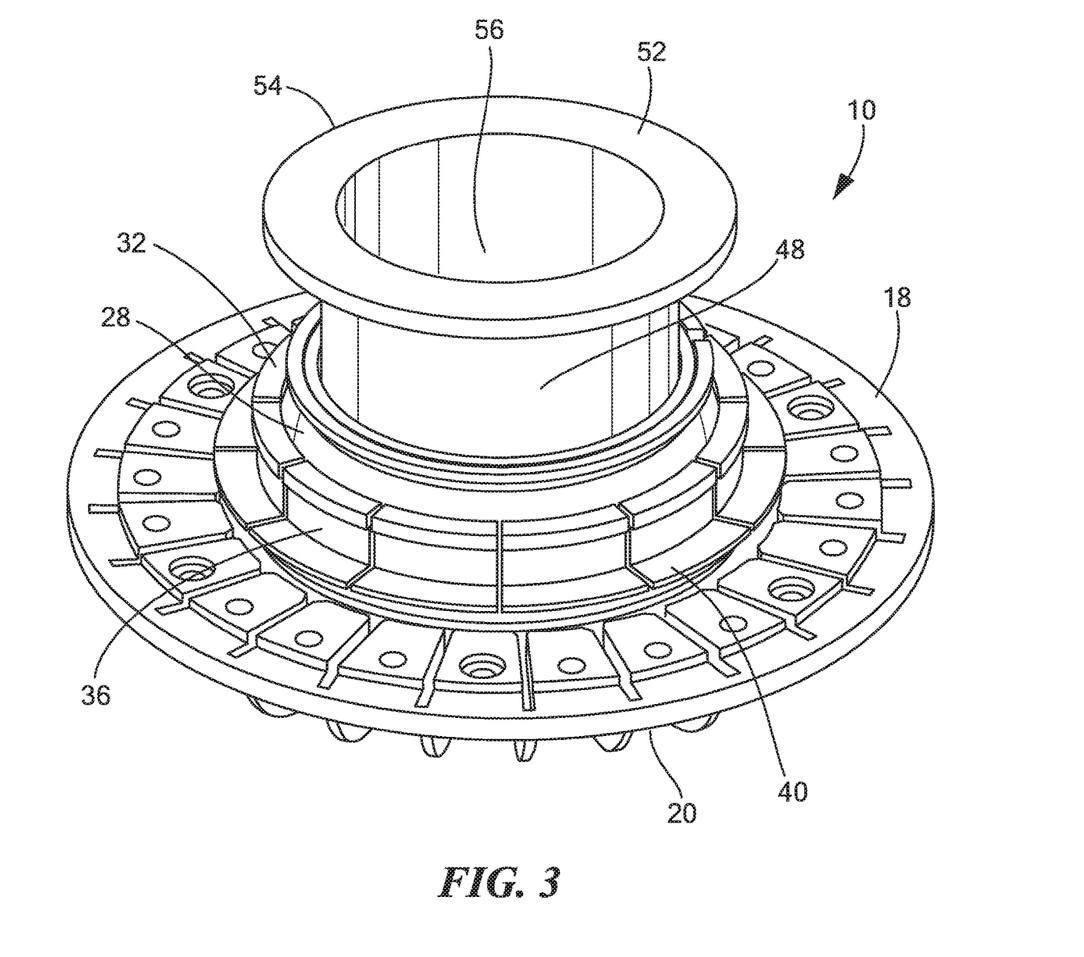
FIG. 3 is a perspective view of the assembled mounting kit shown in FIG. 1 with the plug shown in FIG. 1 partially inserted within the one way valve.
Figure 4:
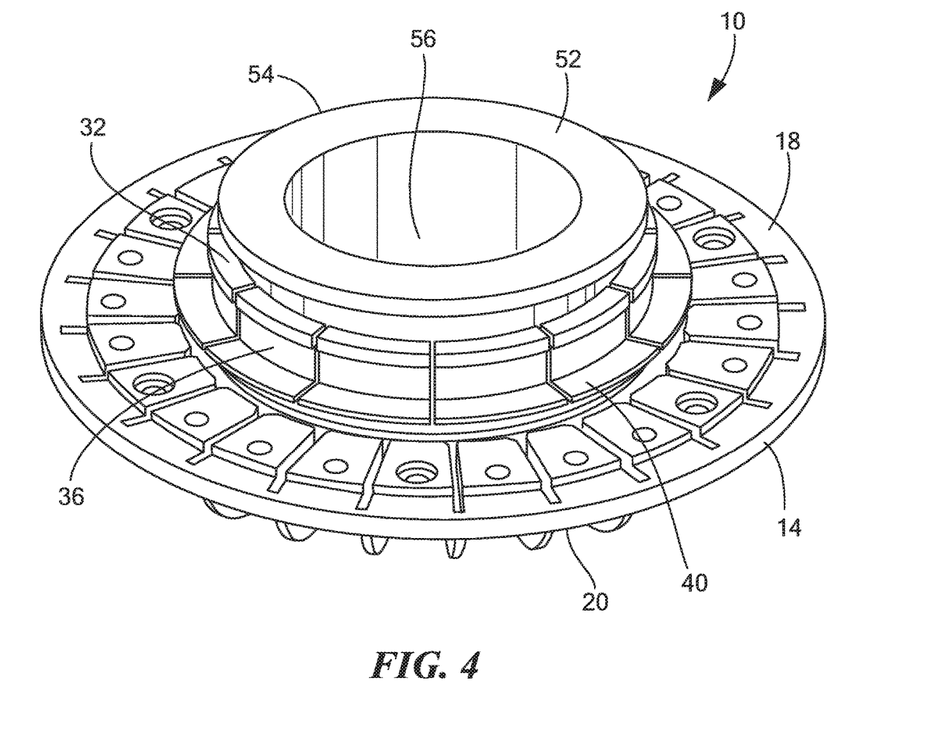
FIG. 4 is a perspective view the assembled view of the mounting kit shown in FIG. 3 with the plug fully inserted through the valve.

Referring now to FIG. 3, after the mounting element 12 is affixed to the exterior of the target tissue or organ, the plug 48 is inserted into the interior of valve 44 with the distal end 58 of the plug 48 contacting the leaves 46 and urges them out of the closed position into the open position. As shown in FIG. 4, when the plug 48 is fully inserted, a substantially unobstructed opening through the mounting element 12 is established within the lumen 56 of the plug 48. Moreover, when the plug 48 is fully inserted, the flange 52 on the plug 48 may contact the gimbal 26 to provide tactile feedback to the user that the plug is fully seated in the valve 44, and to arrest the advance of the plug. In particular, when the plug 48 is fully inserted, the distal end 58 of the plug 48 is flush or substantially flush with the distal side 20 of the ring 14. In one configuration, the plug 48 may further be friction fit within the bore of the mounting element 12.

In an exemplary installation of the mounting kit 10 to the left ventricle of the heart, the plug 48 may be inserted through the valve 44 and into the bore defined mounting element 12. The mounting element 12 may be secured to the exterior surface of the heart. These steps can be performed in any order. Thus, the plug 48 may be inserted within the mounting element 12 before or after the mounting element 12 is affixed to the heart.

Once the mounting element 12 is secured in place on the heart and the plug 48 has been inserted through the valve 44 and into the bore of the mounting element 12, a surgeon may make an incision through the wall of the heart, for example, by making a cruciate cut, through the lumen 56 of the plug 48. The surgeon may make the cruciate cut by hand (e.g. using a scalpel or similar cutting tool) or through the use of a cutting device 60 such as that disclosed in U.S. Patent Publication No. 2007/0167969 the disclosure of which is incorporated by reference herein. In one configuration, because the plug 48 urges the leaves 46 of the valve 44 into the open position, the plug 48 operates to protect the valve 44 from damage during formation of the cruciate cut.

Once the incision into the heart is made, the plug 48 may be removed, thereby allowing the leaves 46 to transition back to their biased closed configuration. The leaves 46 substantially occlude the bore of the mounting element 12 to prevent blood or other material from flowing through the bore when in the closed configuration. A coring tool (not shown) such as that disclosed in pending U.S. Patent Publication No. 2009/012552, the disclosure of which is incorporated by reference herein, may then be inserted through the valve 44 to core the tissue and form a hole in the heart wall. The plug 48 may remain in place while the coring tool is used, if desired. In other embodiments, the coring tool may have a rounded leading end such that it may be inserted through the valve 44 without the need for the plug 48. Once the hole has been formed, an MCSD can be connected to the heart through the hole in the heart wall. For example, the pump of the MCSD, or an inlet cannula connectable to the pump, may be inserted into the bore of the mounting element 12 and secured in place by the mounting element 12, for example, by the adaptor 24. The mounting element 12, valve 44, plug 48, a cutting device 60, and the coring tool may be included in a kit for providing access through tissue. The kit may also include an MCSD and although illustrated for use in the heart, may be used and configured for us with any organ or tissue in the body for insertion of an implant.

Figure 5:
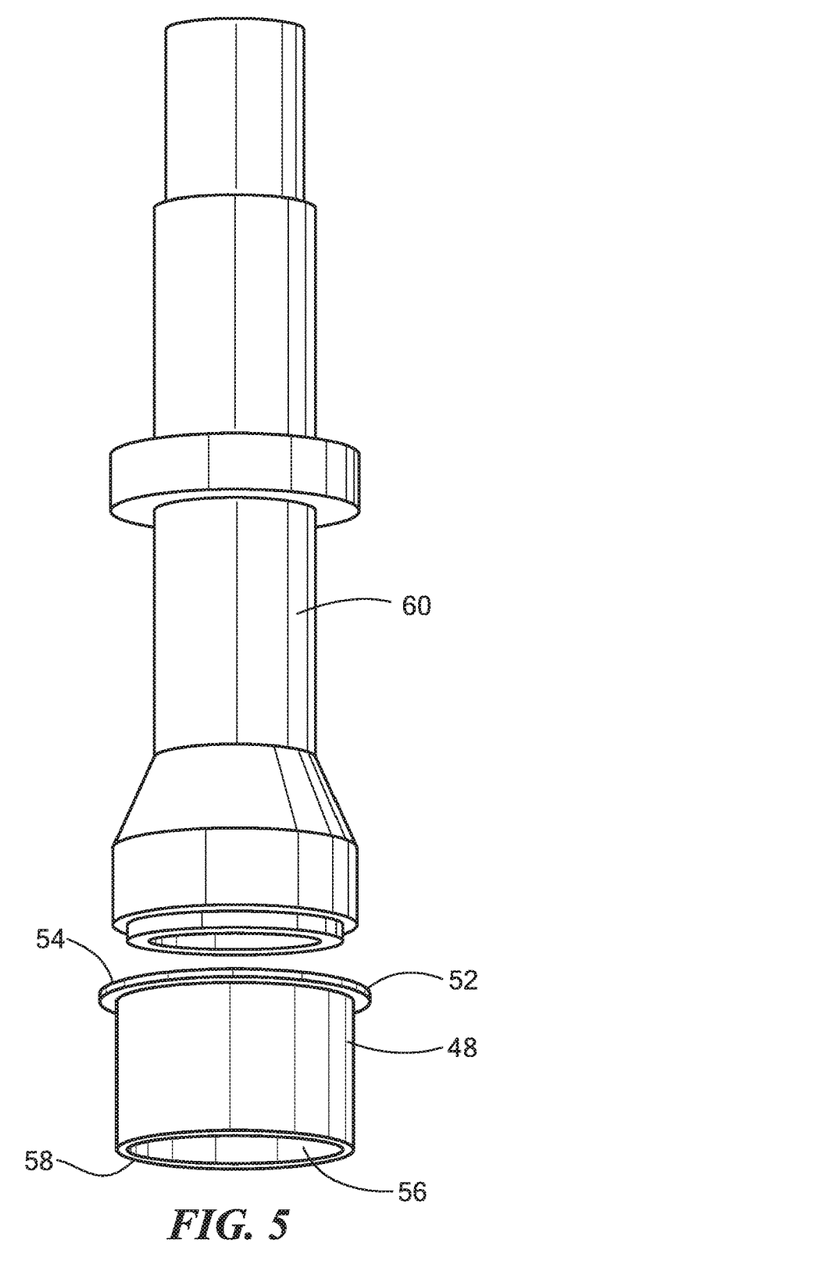
FIG. 5 is perspective view of a coring element with an exemplary plug of the present application coupled to the distal end of the coring element.

Now referring to FIG. 5, the plug 48 may be carried on the cutting device 60 used to make the cruciate cut. For example, the cutting device 60 may include a hollow plug 62 similar to the plug 48 discussed above, mounted on the distal end body of the cutting device 60 so that the plug 62 projects distal to the blade as the cutting device 60 is advanced into and through the mounting element 12. The plug 62 may force the valve 44 into an open position as the plug 62 is inserted into the bore of the mounting element 12, so that the lumen 56 of the plug 62 provides a clear path for movement of the blade associated with the cutting device 60 and formation of the cruciate cut. In a further variant, plug 62 may be slideably mounted on the body of the cutting device 60 and may be moved by, for example, an actuator on the cutting device 60 from a proximal position along the body of the cutting device 60 to a distal position on the body of the cutting device 60 which may force the leaves 46 into the open position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A mounting kit, comprising:
   a mounting element defining a bore, the mounting element being configured to mount to an exterior surface of an organ of a patient;
   a one way valve sized to be received and retained within the bore of the mounting element, the one way valve having an open position and a closed position, the one way valve substantially occluding the bore when the valve is in the closed position, the one way valve being biased in the closed position; and
   a plug having a lumen extending there through, the plug being configured to be releasably inserted through at least a portion of the one way valve, the plug being configured to transition the one way valve from the closed position to the open position and to maintain the one way valve in the open position when the plug is inserted within the bore; the plug is configured to releasably mount to a cutting device.

2. The mounting kit of claim 1, wherein the plug has a flange configured to provide for a maximum depth insertion of the plug within the bore.

3. The mounting kit of claim 1, wherein the one way valve is one from the group consisting of a tri-leaflet valve, flap valve, butterfly valve, and duckbill valve.

4. The mounting kit of claim 1, wherein the mounting element includes a ring defining an opening, the ring being configured to be anchored to the exterior surface of the organ.

5. The mounting kit of claim 4, wherein the mounting element includes an adaptor sized to be received within the opening of the ring, the adaptor defining an aperture, the opening of the ring being substantially co-axial when then adapter is received within the opening of the ring.

6. The mounting kit of claim 5, wherein the adaptor defines an annular wall defining a plurality of slits, and wherein at least a portion of the annular wall is flexible.

7. The mounting kit of claim 6, wherein the adaptor is configured to receive and retain at least one from the group consisting of a pump and a cannula within the bore.

8. The mounting kit of claim 5, wherein the mounting element further includes gimbal sized to be received and retained within the aperture of the adaptor, the gimbal defining an orifice, the gimbal being configured to tilt the alignment of the orifice with respect to the aperture of the adaptor when the gimbal is received within the aperture of the adaptor.

9. The mounting kit of claim 8, wherein the gimbal is substantially co-axial to the adaptor when the gimbal is received within the aperture of the adaptor.

10. The mounting kit of claim 8, wherein the gimbal defines an outer wall surrounding the orifice, and wherein at least a portion of the outer wall is flexible.

11. The mounting kit of claim 1, wherein the organ is the heart.

12. A method of creating an access way into the heart, comprising:
    mounting a mounting element to external surface of the heart, the mounting element defining a bore sized to receive a one way valve disposed therein, the one way valve defining an open position and a closed position, the one way valve substantially occluding the bore when the valve is in the closed position, the valve being biased in the closed position;
    inserting a plug through the one way valve, the plug defining a lumen there through and configured to transition the one way valve from the closed position to the open position and to maintain the one way valve in the open position when the plug is inserted within the bore;
    advancing a cutting device having the plug releaseably coupled to its distal end through the bore; and
    cutting the external surface of the heart through the lumen of the plug.

13. The method of claim 12, further including removing the plug from the bore after cutting the external surface of the tissue and transitioning the one way valve from the open position to the closed position.

14. The method of claim 12, wherein the plug has a flange configured to provide for a maximum depth insertion of the plug within the bore.

15. The method of claim 14, wherein inserting the plug further includes inserting the plug until the flange is pressed against the one way valve.

16. The method of claim 12, wherein the mounting element further includes an adaptor defining an aperture sized to be received within the bore, the adaptor being configured to receive and retain at least one from the group consisting of a pump and a cannula within the bore.

17. The method of claim 16, wherein the mounting element further includes a gimbal defining an orifice, the gimbal being sized to be received within the bore, the gimbal being configured to tilt the alignment of the orifice with respect to the aperture of the adaptor when the gimbal is received within the aperture of the adaptor.

18. A mounting kit, comprising:
    a ring defining an opening, the ring being configured to be anchored to the exterior surface of the left ventricle of a user's heart;
    an adaptor defining an aperture, the adaptor being sized to be received within the opening of the ring, the adaptor being configured to receive and retain at least one from the group consisting of a pump and a cannula within the bore;
    a gimbal defining an orifice, the gimbal being sized to be received within the aperture of the adaptor, the gimbal being configured to tilt the alignment of the orifice with respect to the aperture of the adaptor when the gimbal is received within the aperture of the adaptor, the ring, the adaptor, and the gimbal being substantially co-axial when the adaptor is inserted within the opening of the ring, and the gimbal is inserted within the aperture of the adaptor;

a one way valve sized to be received and retained within orifice of the gimbal, the one way valve having an open position and a closed position, the one way valve substantially occluding the opening, the aperture, and the orifice when the valve is in the closed position, the one way valve being biased in the closed position; and a plug having a lumen extending there through, the plug being configured to be releasably inserted through at least a portion of the one way valve, the plug being configured to transition the one way valve from the closed position to the open position and to maintain the one way valve in the open position when the plug is inserted within the valve, the plug includes a flange configured to provide for a maximum depth insertion of the plug within the valve; the plug is configured to releasably mount to a cutting device.

\* \* \* \* \*